(12) United States Patent
Leifheit et al.

(10) Patent No.: US 6,264,963 B1
(45) Date of Patent: Jul. 24, 2001

(54) SKIN CARE COMPOSITION WITH IMPROVED SKIN HYDRATION CAPABILITY

(76) Inventors: David H. Leifheit, 1840 Brandon La., Racine, WI (US) 53406; David M. Buri, 2115 N. Cape St., Union Grove, WI (US) 53182

(*) Notice: Subject to any disclaimer, the term of this patent is extended or adjusted under 35 U.S.C. 154(b) by 0 days.

(21) Appl. No.: 09/346,273

(22) Filed: Jul. 1, 1999

Related U.S. Application Data

(63) Continuation of application No. 08/984,010, filed on Dec. 3, 1997.

(51) Int. Cl.$^7$ .............................. A61K 6/00; A61K 31/74
(52) U.S. Cl. ...................... 424/401; 424/78.02; 514/886; 514/887
(58) Field of Search ................................ 424/401, 78.02; 514/886, 887

Primary Examiner—Theodore J. Criares
Assistant Examiner—Jennifer Kim

(57) ABSTRACT

An improved skin care composition having enhanced skin hydration, moisturizing, conditioning, and cosmetically acceptable tactile properties. The composition includes a skin hydration system comprising glycerin and plant-derived oil; petrolatum or mineral oil; a di-lower alkyl di-higher alkyl ammonium emulsifier; a fatty alcohol; a fatty ester emollient; and water. Additional components include a humectant system and a lubricant.

26 Claims, No Drawings

SKIN CARE COMPOSITION WITH IMPROVED SKIN HYDRATION CAPABILITY

This application is a continuation of Ser. No. 08/984,010 filed Dec. 3, 1997.

BACKGROUND OF THE INVENTION

1. Field of the Invention

This invention relates to skin care compositions, and in particular, to improved skin care compositions for enhancing skin hydration and for providing excellent moisturizing, conditioning, and cosmetically acceptable tactile properties to the skin.

2. Background of the Related Art

Consumers have long desired hand and body lotions or creams which, when applied to the skin, provide cosmetically acceptable tactile properties. In response to this desire, lotions and creams have been formulated through the years to exhibit satisfactory feel, lubricity, and absorption upon application to the skin.

More recently, consumers have been introduced to specialty lotions and creams formulated to treat dry skin conditions. These specialty lotions and creams hereafter will be referred to as "dry skin formulations."

A particular dry skin formulation is set forth in U.S. Pat. No. 4,389,418 (the '418 patent), which is commonly assigned to the assignee of this application. The '418 patent is hereby incorporated by reference in its entirety.

The dry skin formulation of the '418 patent employs petrolatum or mineral oil as an occlusive agent, and glycerin as a humectant, in combination with a unique di-lower alkyl di-higher alkyl ammonium emulsifier, a fatty alcohol stabilizer, and a fatty ester emollient. As used herein, "occlusive agent" refers to any substance that physically prevents or reduces moisture loss from the skin by formation of a water-impenetrable barrier over the stratum corneum; "humectant" refers to any substance that chemically attracts and holds water to the outside surface and upper layers of the stratum corneum; "stratum corneum" refers to the outer exposed layer of the epidermis.

The dry skin formulation of the '418 patent exhibits excellent moisturizing and conditioning ability upon application to the skin. As used herein, "moisturizing ability" means the ability to increase the water content of the skin, and "conditioning ability" means the ability to improve consumer perception of skin softness and smoothness.

Our invention is directed to improving the moisturizing ability of the dry skin formulation of the '418 patent. We have discovered that increasing the amount of glycerin in this formulation and adding a small amount of plant-derived oil, both within specific ranges of weight percentages or weight ratios, results in an improved cosmetic formulation that synergistically and unexpectedly provides superior short-term skin hydration. As used herein, "skin hydration" refers to the relative water level present in the stratum corneum, as measured by an analytical instrument, such as a Nova DPM dermal phase meter; "short-term skin hydration" refers to the level of skin hydration effected between about 1 and about 12 hours after application of a formulation.

The cosmetics industry has long recognized vegetable (or plant-derived) oils as occlusive agents for reducing transepidermal water loss (hereafter "TEWL"). Recently, vegetable oils have gained popularity, due to the recognition that they provide other usefull cosmetic properties. However, prior to this invention, plant-derived oils had not been recognized for their significant ability to effect short-term skin hydration.

For example, U.S. Pat. No. 5,690,947 (hereafter "the '947 patent") discloses the use of borage seed oil in cosmetic compositions containing hydroxy acids and/or retinoids. The '947 patent only teaches the use of borage seed oil as an anti-irritant to ameliorate skin irritations commonly associated with the use of hydroxy acids and retinoids. This patent does not suggest using borage seed oil to enhance short-term skin hydration.

U.S. Pat. No. 5,620,692 (hereafter "the '692 patent") discloses the use of oat oil in cosmetic compositions to provide beneficial dermatological properties, such as UV-inhibition and anti-oxidancy, in addition to TEWL reduction. The '692 patent, though, does not suggest using oat oil to promote short-term skin hydration.

U.S. Pat. No. 4,375,480 (hereafter "the '480 patent") discloses a hypoallergenic facial skin emulsion having 8–35 parts by weight unsaturated vegetable oil. The vegetable oil serves as an emollient and a moisturizer, and most preferably is sesame oil. Unlike the present invention, the '480 patent does not suggest using vegetable oil to increase short-term skin hydration. Further, the '480 patent requires flushing the skin with water for 2 to 3 minutes immediately after application of the emulsion, in order to effect water absorption into the skin via the emulsion.

U.S. Pat. No. 5,656,278 (hereafter "the '278 patent") discloses dermatological and cosmetic compositions for restoring the barrier function of the stratum corneum. The compositions of this patent require the combination of at least one ceramide, as disclosed therein, and linoleic acid, to effect barrier function restoration. The linoleic acid is preferably obtained from vegetable oils rich in this fatty acid. However, the '278 patent does not disclose or suggest the use of linoleic acid, either alone or in combination with humectants, to improve short-term skin hydration.

U.S. Pat. No. 5,643,899 (hereafter "the '899 patent") discloses various lipid combinations useful for effecting epidermal moisturization and for repairing the barrier function of the stratum corneum. Some of the combinations include essential fatty acids, such as linoleic acid, as a component. Vegetable oils containing the required essential fatty acids may be used in the lipid combinations. Unlike the present invention, the '899 patent requires all of the lipids set forth therein, including vegetable oils, to be used in combination with at least one other non-vegetable-derived lipid. Moreover, the '899 patent does not disclose or suggest using vegetable oil to provide enhanced short-term skin hydration.

U.S. Pat. No. 4,740,367 (hereafter "the '367 patent") discloses the use of a vegetable oil adduct, produced by the Diels-Alder reaction with fumaric, maleic anhydride or acrylic aid, or a combination of the vegetable oil adduct and its parent vegetable oil, as an emollient/moisturizer in skin and hair compositions. The '367 patent suggests, as a preferred combination, soybean oil-fumaric acid adduct and soybean oil. However, the '367 patent does not disclose or suggest the use of vegetable oil, either alone or in combination with other humectants, to enhance short-term slin hydration.

U.S. Pat. No. 5,229,130 (hereafter "the '130 patent") relates to methods and compositions for enhancing skin permeation of pharmaceutically active agents across the stratum corneum. The skin permeation enhancing component is a vegetable oil, which preferably does not contain large amounts of saturated fatty acids or fatty acids having less than 8 or greater than 14 carbon atoms. The '130 patent prefers a combination of coconut and soybean oils. The '130 patent, however, does not disclose or suggest the utility of vegetable oils for enhancing skin permeation of water.

U.S. Pat. No. 4,632,772 (hereafter "the '772 patent") discloses an anti-microbial detergent composition having 2.2 to 14 parts by weight moisturizer/emollient as a component. The moisturizer/emollient may comprise a vegetable oil. Unlike the present invention, the moisturizer/emollient of the '772 patent functions to replace the natural skin oils which are lost or partially removed by the detergent composition. The '772 patent does not discloses or suggest using vegetable oil to provide enhanced short-term skin hydration.

SUMMARY OF THE INVENTION

An object of the present invention is to provide a cosmetic composition with significantly improved moisturizing ability, as well as excellent conditioning ability and cosmetically acceptable tactile properties. This invention is based upon the finding that increasing the amount of glycerin and adding a small quantity of plant-derived oil, both within particular ranges of weight percentages or weight ratios, in the formulation of the '418 patent, provides an improved composition, which upon application to the skin results in synergistic and unexpectedly superior short-term skin hydration.

In one aspect of our invention, an improved skin care composition comprises a skin hydration system, in an amount between about 16 and about 22 weight percent of the composition, comprising glycerin and plant-derived oil in amounts sufficient to maintain a weight ratio of said glycerin to said plant-derived oil in the range between about 13:1 and about 36:1; petrolatum or mineral oil, in an amount between about 1 and about 10 weight percent of the composition; a quaternary ammoniun emulsifier, in an amount between about 2 and about 12 weight percent of the composition, having the formula

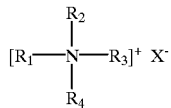

wherein $R_1$ and $R_2$ are each long chain, substantially linear alkyl groups having from about 16 to 22 carbon atoms, $R_3$ and $R_4$ are each lower alkyl groups having from about 1 to 3 carbon atoms and X is a salt-forming anion; a fatty alcohol, in an amount between about 1.5 and about 5 weight percent of the composition; a fatty ester emollient, in an amount between about 1 and about 8 weight percent of the composition; and water, in an amount between about 25 and about 95 weight percent of the composition.

In another aspect, the improved skin care composition of this invention further comprises a humectant system, in an amount sufficient to maintain a weight ratio of said glycerin and said humectant system to said plant-derived oil in the range between about 18:1 to about 59:1. The humectant system includes preferably at least one compound selected from sodium pyrrolidone carboxylate, beta-glucan, lactic acid, and lactic acid salts.

In still another aspect of our invention, an improved skin care composition comprises a skin hydration system comprising glycerin, in an amount between about 16 and about 19 weight percent of the composition, and plant-derived oil, in an amount between about 0.5 and about 1.5 weight percent of the composition; petrolatum or mineral oil, in an amount between about 1 and about 10 weight percent of the composition; a quaternary ammonium emulsifier, in an amount between about 2 and about 12 weight percent of the composition, having the formula

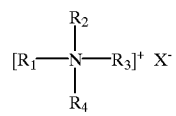

wherein $R_1$ and $R_2$ are each long chain, substantially linear alkyl groups having from about 16 to 22 carbon atoms, $R_3$ and $R_4$ are each lower alkyl groups having from about 1 to 3 carbon atoms and X is a salt-forming anion; a fatty alcohol, in an amount between about 1.5 and about 5 weight percent of the composition; a fatty ester emollient, in an amount between about 1 and about 8 weight percent of the composition; and water, in an amount between about 25 and about 95 weight percent of the composition.

In another aspect, the improved skin care composition of this invention further comprises a humectant system, in an amount up to about 8 weight percent of the composition. The humectant system includes preferably at least one compound selected from sodium pyrrolidone carboxylate, beta-glucan, lactic acid, and lactic acid salts.

In yet another aspect of our invention, an improved skin care composition comprises a skin hydration system comprising glycerin, in an amount between about 18 and about 20 weight percent of the composition, and plant-derived oil, in an amount between about 1 and about 1.5 weight percent of the composition; petrolatum or mineral oil, in an amount between about 1 and about 10 weight percent of the composition; a quaternary ammonium emulsifier, in an amount between about 2 and about 12 weight percent of the composition, having the formula

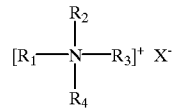

wherein $R_1$ and $R_2$ are each long chain, substantially linear alkyl groups having from about 16 to 22 carbon atoms, $R_3$ and $R_4$ are each lower alkyl groups having from about 1 to 3 carbon atoms and X is a salt-forming anion; a fatty alcohol, in an amount between about 1.5 and about 5 weight percent of the composition; a fatty ester emollient, in an amount between about 1 and about 8 weight percent of the composition; and water, in an amount between about 25 and about 95 weight percent of the composition.

In another aspect, the improved skin care composition of this invention further comprises a humectant system, in an amount up to about 8 weight percent of the composition. The humectant system includes preferably at least one compound selected from sodium pyrrolidone carboxylate, beta-glucan, lactic acid, and lactic acid salts.

Other aspects of this invention will be better understood and advantages thereof more apparent in view of the following detailed description of the preferred embodiments.

DETAILED DESCRIPTION OF THE PREFERRED EMBODIMENTS

The improved dry skin formulation of the present invention comprises:

(1) a skin hydration system;

(2) petrolatun or mineral oil;

(3) di-lower alkyl di-higher alkyl ammonium emulsifier;

(4) fatty alcohol;

(5) fatty acid emollient; and
(6) water.

The improved dry skin formulation of the present invention may additionally include:

(7) a humectant system; and
(8) a lubricant.

Optional components include those typically employed in the field, including, but not limited to, fragrances, dyes, preservatives, sun screen additives, skin protectants, and medicaments.

Each of these components is discussed in greater detail, as follows.

Skin Hydration System

The skin hydration system of the present invention comprises glycerin and plant-derived oil. The plant-derived oil comprises preferably oat lipid extract (otherwise known as oat oil), borage oil, or combinations thereof. Plant-derived oils with structures similar to oat oil and borage oil may also be used.

The skin hydration system is specified preferably in terms of weight percentages of glycerin and plant-derived oil. In a preferred skin hydration system, glycerin comprises preferably between about 16 and about 19 weight percent of the composition, and plant-derived oil comprises preferably between about 0.5 and about 1.5 weight percent of the composition, more preferably between about 0.75 and about 1.25 weight percent of the composition, and most preferably about 1 weight percent of the composition. In another preferred skin hydration system, glycerin comprises preferably between about 18 and about 20 weight percent of the composition, and plant-derived oil comprises preferably between about 1 and about 1.5 weight percent of the composition, more preferably between about 1 and about 1.25 weight percent of the composition, and most preferably about 1 weight percent of the composition.

The skin hydration system also can be specified in terms of weight ratios of glycerin to plant-derived oil. In a preferred embodiment, the skin hydration system comprises between about 16 and about 22 weight percent of the composition, and includes glycerin and plant-derived oil in amounts sufficient to maintain a weight ratio of glycerin to plant-derived oil in the range preferably between about 13:1 and about 36:1, more preferably between about 18:1 and about 32:1, and most preferably between about 18:1 and about 20:1. In another preferred embodiment, the skin hydration system comprises between about 17 and about 20 weight percent of the composition, and includes glycerin and plant-derived oil in amounts sufficient to maintain the same preferred weight ratios as the previous preferred embodiment.

We have found that glycerin and plant-derived oil must be present within the above-described ranges of weight percentages or weight ratios, in order to provide synergistic and superior short-term skin hydration levels. We have found that using either increased amounts of glycerin or plant-derived oil alone in the present invention does not provide statistically significant differences in short-term skin hydration relative to the dry skin formulation of the '418 patent.

The synergistic and superior short-term skin hydration levels achieved by our invention is surprising, because while glycerin might reasonably have been expected to increase skin hydration, the use of plant-derived oil, even as a moisturizer, would only have been expected to provide long-term skin hydration (i.e., after 24 hours). Further, it would not have been apparent to one of ordinary skill to employ such a small amount of plant-derived oil, as required in the present invention, to effect significant increases in skin hydration, either short-term or long-term.

Petrolatum or Mineral Oil

The petrolatum suitable for use in the present invention comprises any grade of white or yellow petrolatum which is recognized as being safe for application to the human skin. The preferred types are petrolatum U.S.P. XVIII or NFXII. In general, any viscosity or consistency grade of petrolatum recognized in the art can be employed in this invention. It is within the scope of our invention to partially replace petrolatum with mixtures of hydrocarbon materials which can be formulated to resemble petrolatum in appearance and consistency. For example, such a combination can be formed by melting mineral oil in various proportions with substances such as, for example, microcrystalline wax, paraffin wax and the like.

The mineral oil employed in this invention should be USP or NF grade white mineral oils and should preferably have a viscosity of about 6.7 to about 69 cst at 40 C., a specific gravity (SG 15.6 C./15.6 C.) of about 0.828 to about 0.890, and a maximum pour point of about −18 C to about −7 C. More preferably, the mineral oils should have a viscosity of about 6.7 to about 17.0 cst at 40 C., a specific gravity of about 0.828 to about 0.860, and a maximum pour point of about −7 C to about −10 C.

Petrolatum and mineral oil, either alone or in combination with the other, comprises preferably between about 1 and about 10 weight percent of the composition, more preferably between about 1 and about 6 weight percent of the composition, and most preferably between about 3 and about 5 weight percent of the composition.

Di-lower Alkyl Di-higher Alkyl Ammonium Emulsifier

The di-lower alkyl di-higher alkyl ammonium emulsifiers of this invention have the general formula:

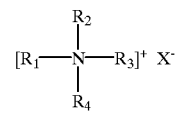

wherein $R_1$ and $R_2$ are each long chain, substantially linear alkyl groups having from about 16 to about 22 carbon atoms, $R_3$ and $R_4$ are each lower alkyl groups having from about 1 to about 3 carbon atoms, and X is a salt-forming anion. Preferably the salt forming anion is chloride, bromide, or iodide.

These quaternary ammonium emulsifiers preferably exhibit hard, waxy and nonstick characteristics. In general, when long chain alkyl groups below $C_{16}$, ethoxylated cationics or mono long chain alkyl groups are employed, the viscosity of the resulting formulation is reduced to an unacceptable level.

In addition to their emulsifying, skin softening and skin protective properties, the quaternary ammonium emulsifiers of our invention are believed to provide still another unique feature upon application to the skin. As cationic surfactants, quaternary ammonium emulsifiers carry positive charges. In general, detergents and soaps are anionic and carry negative charges. Uncomplexed residual soaps and detergents can induce irritation. Application of cationic emulsifiers should prevent this irritation from occurring, due to the formation of insoluble complexes between the cationic emulsifiers and the residual soaps and detergents on the skin.

The di-lower alkyl di-higher alkyl ammonium emulsifiers of our invention comprise preferably between about 2 and about 12 weight percent of the composition, more preferably between about 2 and about 7 weight percent of the composition, and most preferably between about 4 and about 6 weight percent of the composition.

A preferred emulsifier is distearyl dimethyl ammonium chloride (hereafter "DSDMAC").

Fatty Alcohol

The fatty alcohol employed in the present invention assists in stabilizing the emulsion and in providing cosmetically acceptable viscosity for the composition. In general, a $C_{14}$ to $C_{22}$ substantially saturated alkanol is employed. Typical examples of suitable fatty alcohols include stearyl alcohol, myristyl alcohol, behenyl alcohol, arachidic alcohol, isostearyl alcohol and isocetyl alcohol. We prefer to employ cetyl alcohol. If desired, cetyl alcohol may be employed alone or in combination with other fatty alcohols, particularly, isostearyl alcohol.

The fatty alcohol comprises preferably between about 1.5 and about 5 weight percent of the composition, more preferably between about 1.5 and about 3 weight percent of the composition, and most preferably between about 2 and about 3 weight percent of the composition.

Fatty Ester Emollient

The fatty ester emollient of the invention is employed in sufficient amounts to enhance the tactile properties of the composition. In particular, fatty esters assist in softening the base formulation of petrolatum, quaternary ammonium emulsifier, and fatty alcohol. Typical fatty esters employed in the present invention include isopropyl myristate, isopropyl palnitate, isopropyl isostearate, isostearyl isostearate, diisopropyl sebacate, propylene glycol dipelargonate, 2-ethyl-hexyl isononoate, 2-ethylhexyl stearate, $C_{12}$–$C_{16}$ fatty alcohol lactate, isopropyl lanolate, 2-ethyl-hexyl salicylate and mixtures thereof.

The fatty ester emollient comprises preferably between about 1 and about 8 weight percent of the composition, more preferably between about 1 and about 5 weight percent of the composition, and most preferably between about 2 and about 4 weight percent of the composition.

Water

The amount of water to be included in the compositions of the invention varies depending upon the desired consistency of the final product. Since the compositions of the invention are oil-in-water emulsions, it is possible, by varying the amount of water present, to formulate, for example, a thick-flowing liquid or lotion, a semiliquid thick cream, a paste and the like.

We prefer to employ deionized water.

Water comprises preferably between about 25 and about 95 weight percent of the composition, more preferably between about 40 and about 70 weight percent of the composition, and most preferably between about 50 and about 65 weight percent of the composition Humectant System If desired, a humectant system may additionally be present in the composition of the present invention. The humectant system comprises preferably at least one compound selected from the group consisting of sodium pyrrolidone carboxylate (hereafter "SPC"), beta-glucan, lactic acid, and lactic acid salts. Preferred lactic acid salts include sodium lactate and ammonium lactate. A preferred source of beta-glucan is colloidal oat bran.

The humectant system comprises preferably up to about 8 weight percent of the composition, more preferably between about 1 and about 8 weight percent of the composition, and most preferably between about 1 and about 7 weight percent of the composition.

The humectant system may also be specified in terms of weight ratios of glycerin and humectant system to plant-derived oil. In a preferred embodiment, the humectant system is present in an amount sufficient to maintain a weight ratio of the glycerin and the humectant system to plant-derived oil in the range preferably between about 18:1 and about 59:1, more preferably between about 19:1 and about 38:1, and most preferably between about 20:1 and about 26:1.

Lubricant

In order to improve the lubricity of the composition during application, it is desirable to employ a silicone oil or fluid, such as dimethylpolysiloxane or other conventional polysiloxane, as a lubricant. In general, the viscosity of the silicone oil at a temperature of 25 C. is from about 5 centistokes to about 12,500 centistokes. Typical polysiloxanes employed in the invention include dimethylpolysiloxane, dimethyl polysiloxane end blocked with trimethyl units (CTFA name dimethicone), diethylpolysiloxane, dimethylpolysiloxane-diphenylpolysiloxane, cyclomethicone, trimethylpolysiloxane, diphenylpolysiloxane, and mixtures thereof.

A preferred lubricant is dimethicone.

The lubricant comprises preferably up to about 5 weight percent of the composition, more preferably between about 0.1 and about 3 weight percent of the composition, and most preferably between about 1 and about 2 weight percent of the composition.

Optional Components

Other conventional additives typically employed in cosmetic compositions may be utilized as optional components. Fragrance oils, which mask the odor of the base and provide cosmetic appeal, can be employed. Nontoxic and compatible dyes may be utilized to color the composition, as desired. Preservatives, such as methylparaben or other esters of parahydroxy benzoic acid, can be employed. If desired, formaldehyde and like preservatives can also be utilized.

In addition, a sun screen additive, such as octyl dimethyl para-aminobenzoic acid can be employed in the inventive composition in amounts from about 1 to about 8 weight percent of the composition. To provide a skin protectant composition, zinc oxide and like ingredients can be provided in amounts from about 0.5 to about 3 weight percent of the composition. As a medicament, various essential oils, such as menthol and the like, and vitamin oils can be employed in amounts from 0.1 to about 2 weight percent of the composition.

Additionally, minor amounts of other conventional emollients, emulsifiers, thickeners or other cosmetic additives can be employed.

The compositions of our invention are prepared according to methods well-known to those of ordinary skill, and are not limited to any specific manufacturing process. The compositions of the present invention can be prepared, generally, by dispersing the fatty alcohol, vegetable oil, and quaternary ammonium emulsifier into the petrolatum or mineral oil. The resulting dispersion is heated to a temperature of from about 170 F. to about 190 F. under agitation to form a hot oil phase. The water and optional colorants and preservatives are admixed and heated to a temperature of from about 170 F. to about 190 F. under agitation to form a hot aqueous phase. Next, the hot oil phase is added to the hot aqueous phase, and the resulting dispersion is agitated until a homogeneous mixture is obtained.

The mixture is then cooled to a temperature of about 90 F. and fragrance is added under agitation until a homogeneous product is obtained. Depending upon the quantity of water employed, a homogeneous lotion, cream, or paste can be produced.

The skin care compositions of the present invention are topically applied in a conventional manner. In general, the compositions may be dispensed from a container and then gently applied to the skin.

EXAMPLES

The following examples set forth below in Tables 1 and 2, namely Examples 1 through 8, illustrate embodiments of the present invention. All amounts are given in weight percent. The present invention is not limited to the examples contained therein. Skin hydration levels, as measured by a Nova DPM dermal phase meter, are provided for each example at 1, 2, 3, 4, 9, and 12 hours after application on human test subjects. AVEENO, a commercial embodiment of the '418 patent, was used as a control. As the results demonstrate, the present invention results in superior and statistically significant increased short-term skin hydration levels.

TABLE 1

| Component | Control | Example 1 | Example 2 | Example 3 | Example 4 | Example 5 |
|---|---|---|---|---|---|---|
| Glycerin | 12 | 18 | 18 | 18 | 18 | 18 |
| Oat Oil | | 1 | 1 | 1 | | 0.5 |
| Borage Oil | | | | | 0.5 | 0.5 |
| Petrolatum | 4 | 4 | 4 | 4 | 4 | 4 |
| DSDMAC | 5 | 5 | 5 | 5 | 5 | 5 |
| Cetyl Alcohol | 2.5 | 2.5 | 2.5 | 2.5 | 2.5 | 2.5 |
| Isopropyl Palmitate | 3 | 2 | 2 | 2 | 2 | 2 |
| Water | 70.64 | 63.84 | 63.77 | 58.34 | 64.54 | 63.44 |
| Lactic Acid, 88% | | | 0.85 | | | |
| Ammonium Lactate | | | 0.42 | 6.7 | | |
| SPC | | 1 | | | 1 | 1 |
| Dimethicone | 1.25 | 1.25 | 1.25 | 1.25 | 1.25 | 1.25 |
| Colloidal Oats | 1 | 1 | 1 | 1 | 1 | 1 |
| Benzyl Alcohol | 0.6 | | | | | 0.6 |
| NaCl | 0.01 | 0.01 | 0.01 | 0.01 | 0.01 | 0.01 |
| DL-Panthenol | | 0.4 | 0.2 | 0.2 | 0.2 | 0.2 |
| TOTAL | 100 | 100 | 100 | 100 | 100 | 100 |

Nova DPM Values (higher value indicates greater skin hydration)

| Hour | Control | Example 1 | Example 2 | Example 3 | Example 4 | Example 5 |
|---|---|---|---|---|---|---|
| 1 | 262 | 316 | 330 | 388 | 326 | 321 |
| 2 | 252 | 319 | 331 | 400 | 315 | 327 |
| 3 | 248 | 324 | 337 | 390 | 323 | 321 |
| 4 | 249 | 333 | 332 | 390 | 323 | 323 |
| 9 | 236 | 333 | 336 | 356 | 326 | 324 |
| 12 | 239 | 318 | 313 | 348 | 320 | 318 |

TABLE 2

| Component | Control | Example 6 | Example 7 | Example 8 |
|---|---|---|---|---|
| Glycerin | 12 | 16 | 16 | 20 |
| Oat Oil | | 0.5 | 0.5 | 1 |
| Petrolatum | 4 | 4 | 4 | 4 |
| DSDMAC | 5 | 5 | 5 | 5 |
| Cetyl Alcohol | 2.5 | 2.5 | 2.5 | 2.5 |
| Isopropyl Palmitate | 3 | 3 | 3 | 3 |
| Water | 70.64 | 59.21 | 57.21 | 55.71 |
| Lactic Acid, 88% | | 2.85 | 2.85 | 2.85 |
| Sodium Lactate, 60% | | 3.08 | 3.08 | 3.08 |
| SPC | | 1 | | |
| Colloidal Oat Bran | | | 3 | |
| Dimethicone | 1.25 | 1.25 | 1.25 | 1.25 |
| Colloidal Oats | 1 | 1 | 1 | 1 |
| Benzyl Alcohol | 0.6 | 0.6 | 0.6 | 0.6 |
| NaCl | 0.01 | 0.01 | 0.01 | 0.01 |
| TOTAL | 100 | 100 | 100 | 100 |

Nova DPM Values (higher value indicates greater skin hydration)

| Hour | Control | Example 6 | Example 7 | Example 8 |
|---|---|---|---|---|
| 1 | 266 | 310 | 294 | 317 |
| 2 | 270 | 311 | 310 | 338 |
| 3 | 272 | 316 | 306 | 332 |
| 4 | 264 | 315 | 307 | 334 |
| 9 | 246 | 299 | 297 | 315 |
| 12 | 237 | 307 | 288 | 311 |

COMPARATIVE TESTING

A preliminary test was conducted to determine the effects of (1) increasing the amount of glycerin (with an addition of a minor amount of oat oil) in the formulation of the '418 patent, and (2) adding oat oil alone to the dry skin formulation of the '418 patent. AVEENO, a commercial embodiment of the '418 patent, was employed as a control. The results are displayed below in Table 3, as Comparative Examples A, B, and C. All component amounts are given in weight percent As the results suggest, merely increasing the amount of glycerin or adding oat oil does not result in statistically significant differences in skin hydration levels relative to the dry skin formulation of the '418 patent.

TABLE 3

| Component | Control | Comparative Example A | Comparative Example B | Comparative Example C |
|---|---|---|---|---|
| Glycerin | 12 | 20 | 12 | 12 |
| Oat Oil | | 0.5 | 0.5 | 1 |
| Petrolatum | 4 | 4 | 4 | 4 |
| DSDMAC | 5 | 5 | 7 | 5 |
| Cetyl Alcohol | 2.5 | 2.5 | 3.5 | 2.5 |
| Isopropyl Palmitate | 3 | 3 | 3 | 3 |
| Water | 70.64 | 60.75 | 59.65 | 63.71 |
| Lactic Acid, 88% | | | 2 | 2.85 |
| Sodium Lactate, 60% | | | 4.5 | 3.08 |
| SPC | | 1 | 1 | |
| Dimethicone | 1.25 | 1.25 | 1.25 | 1.25 |
| Colloidal Oats | 1 | 1 | 1 | 1 |
| Benzyl Alcohol | 0.6 | 0.6 | 0.6 | 0.6 |
| NaCl | 0.01 | | | 0.01 |
| DL-Panthenol | | 0.4 | | |
| TOTAL | 100 | 100 | 100 | 100 |

Nova DPM Values (higher value indicates greater skin hydration)

| Hour | Control | Comparative Example A | Comparative Example B | Comparative Example C |
|---|---|---|---|---|
| 1 | 266 | 267 | 291 | 291 |
| 2 | 270 | 267 | 299 | 299 |
| 3 | 272 | 277 | 300 | 295 |
| 4 | 264 | 293 | 296 | 301 |
| 9 | 246 | 262 | 269 | 282 |
| 12 | 237 | 261 | 272 | 278 |

INDUSTRIAL APPLICABILITY

Any composition of the present invention, including at least the above-described embodiments and formulations, may be used, either alone or in combination with other components, as a skin conditioning lotion, cream, or paste. Gel formulations are also envisioned. The lotion, cream, paste, and gel formulations may be packaged in various dispensing containers designed to promote storage stability of the composition. We also envision that this invention be used as a vehicle for sun screen and insect repellent lotions, creams, pastes, and gels.

While the present invention has been described with respect to what is at present considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent formulations and functions.

We claim:

1. An improved skin care composition having enhanced skin hydration, moisturizing, conditioning, and cosmetically acceptable tactile properties, said composition comprising:

a skin hydration system, in an amount between about 16 and about 22 weight percent of the composition, comprising glycerin and plant-derived oil in amounts sufficient to maintain a weight ratio of said glycerin to said plant-derived oil in the range between about 13:1 and about 36:1;

petrolatum or mineral oil, in an amount between about 1 and about 10 weight percent of the composition;

a quaternary ammonium compound, in an amount between about 2 and about 12 weight percent of the composition, said quaternary ammonium compound having the formula

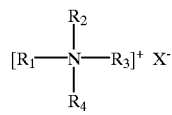

wherein $R_1$ and $R_2$ are each long chain, substantially linear alkyl groups having from about 16 to 22 carbon atoms, $R_3$ and $R_4$ are each lower alkyl groups having from about 1 to 3 carbon atoms and X is a salt-forming anion;

a fatty alcohol, in an amount between about 1.5 and about 5 weight percent of the composition;

a fatty ester emollient, in an amount between about 1 and about 8 weight percent of the composition; and water, in an amount between about 25 and about 95 weight percent of the composition.

2. An improved skin care composition according to claim 1, wherein said plant-derived oil comprises at least one compound selected from the group consisting of oat lipid extract and borage oil.

3. An improved skin care composition according to claim 1, wherein said glycerin and said plant-derived oil are present in amounts sufficient to maintain a weight ratio of said glycerin to said plant-derived oil in the range between about 18:1 and about 32:1.

4. An improved skin care composition according to claim 1, wherein said glycerin and said plant-derived oil are present in amounts sufficient to maintain a weight ratio of said glycerin to said plant-derived oil in the range between about 18:1 and about 20:1.

5. An improved skin care composition according to claim 1, further comprising a humectant system, said humectant system being present in an amount sufficient to maintain a weight ratio of said glycerin and said humectant system to said plant-derived oil in the range between about 18:1 and about 59:1.

6. An improved skin care composition according to claim 5, wherein said humectant system comprises at least one compound selected from the group consisting of sodium pyrrolidone carboxylate, beta-glucan, lactic acid, and lactic acid salts.

7. An improved skin care composition according to claim 5, wherein said humectant system is present in an amount sufficient to maintain a weight ratio of said glycerin and said humectant system to said plant-derived oil in the range between about 19:1 and about 38:1.

8. An improved skin care composition according to claim 7, wherein said humectant system comprises at least one compound selected from the group consisting of sodium pyrrolidone carboxylate, beta-glucan, lactic acid, and lactic acid salts.

9. An improved skin care composition according to claim 5, wherein said humectant system is present in an amount sufficient to maintain a weight ratio of said glycerin and said humectant system to said plant-derived oil in the range between about 20:1 and about 26:1.

10. An improved skin care composition according to claim 9, wherein said humectant system comprises at least one compound selected from the group consisting of sodium pyrrolidone carboxylate, beta-glucan, lactic acid, and lactic acid salts.

11. An improved skin care composition having enhanced skin hydration, moisturizing, conditioning, and cosmetically acceptable tactile properties, said composition comprising:

a skin hydration system comprising glycerin, in an amount between about 16 and about 19 weight percent of the composition, and plant-derived oil, in an amount between about 0.5 and about 1.5 weight percent of the composition;

petrolatum or mineral oil, in an amount between about 1 and about 10 weight percent of the composition;

a quaternary ammonium compound, in an amount between about 2 and about 12 weight percent of the composition, said quaternary ammonium compound having the formula

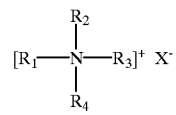

wherein $R_1$ and $R_2$ are each long chain, substantially linear alkyl groups having from about 16 to 22 carbon atoms, $R_3$ and $R_4$ are each lower alkyl groups having from about 1 to 3 carbon atoms and X is a salt-forming anion;

a fatty alcohol, in an amount between about 1.5 and about 5 weight percent of the composition;

a fatty ester emollient, in an amount between about 1 and about 8 weight percent of the composition; and water, in an amount between about 25 and about 95 weight percent of the composition.

12. An improved skin care composition according to claim 11, wherein-said plant-derived oil comprises at least one compound selected from the group consisting of oat lipid extract and borage oil.

13. An improved skin care composition according to claim 11, wherein said plant-derived oil is present in an amount between about 0.75 and about 1.25 weight percent of the composition.

14. An improved skin care composition according to claim 11, wherein said plant-derived oil is present in an amount of about 1 weight percent of the composition.

15. An improved skin care composition according to claim 11, further comprising a humectant system, in an amount up to about 8 weight percent of the composition.

16. An improved skin care composition according to claim 15, wherein said humectant system is present in an amount between about 1 and about 8 weight percent of the composition.

17. An improved skin care composition according to claim 15, wherein said humectant system is present in an amount between about 1 and about 7 weight percent of the composition.

18. An improved skin care composition according to claim 15, wherein said humectant system comprises at least one compound selected from the group consisting of sodium pyrrolidone carboxylate, beta-glucan, lactic acid, and lactic acid salts.

19. An improved skin care composition having enhanced skin hydration, moisturizing, conditioning, and cosmetically acceptable tactile properties, said composition comprising:

a skin hydration system comprising glycerin, in an amount between about 18 and about 20 weight percent of the composition, and plant-derived oil, in an amount between about 1 and about 1.5 weight percent of the composition;

petrolatum or mineral oil, in an amount between about 1 and about 10 weight percent of the composition;

a quaternary ammonium compound, in an amount between about 2 and about 12 weight percent of the composition, said quaternary ammonium compound having the formula

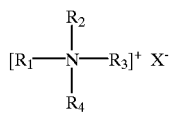

wherein $R_1$ and $R_2$ are each long chain, substantially linear alkyl groups having from about 16 to 22 carbon atoms, $R_3$ and $R_4$ are each lower alkyl groups having from about 1 to 3 carbon atoms and X is a salt-forming anion;

a fatty alcohol, in an amount between about 1.5 and about 5 weight percent of the composition;

a fatty ester emollient, in an amount between about 1 and about 8 weight percent of the composition; and water, in an amount between about 25 and about 95 weight percent of the composition.

20. An improved skin care composition according to claim 19, wherein said plant-derived oil comprises at least one compound selected from the group consisting of oat lipid extract and borage oil.

21. An improved skin care composition according to claim 19, wherein said plant-derived oil is present in an amount between about 1 and about 1.25 weight percent of the composition.

22. An improved skin care composition according to claim 19, wherein said plant-derived oil is present in an amount of about 1 weight percent of the composition.

23. An improved skin care composition according to claim 19, further comprising a humectant system, in an amount up to about 8 weight percent of the composition.

24. An improved skin care composition according to claim 23, wherein said humectant system is present in an amount between about 1 and about 8 weight percent of the composition.

25. An improved skin care composition according to claim 23, wherein said humectant system is present in an amount between about 1 and about 7 weight percent of the composition.

26. An improved skin care composition according to claim 23, wherein said humectant system comprises at least one compound selected from the group consisting of sodium pyrrolidone carboxylate, beta-glucan, lactic acid, and lactic acid salts.

* * * * *